US012746055B2

(12) United States Patent
Takahashi

(10) Patent No.: US 12,746,055 B2
(45) Date of Patent: Sep. 29, 2026

(54) MEDICAL DEVICE AND MEDICAL SYSTEM

(71) Applicant: TERUMO KABUSHIKI KAISHA, Tokyo (JP)

(72) Inventor: Yusuke Takahashi, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 832 days.

(21) Appl. No.: 18/164,033

(22) Filed: Feb. 3, 2023

(65) Prior Publication Data

US 2023/0248421 A1 Aug. 10, 2023

(30) Foreign Application Priority Data

Feb. 4, 2022 (JP) ................................ 2022-016303

(51) Int. Cl.
*A61B 18/14* (2006.01)
*A61B 18/00* (2006.01)

(52) U.S. Cl.
CPC *A61B 18/1482* (2013.01); *A61B 2018/00595* (2013.01); *A61B 2018/00702* (2013.01);
(Continued)

(58) Field of Classification Search
CPC ............ A61B 18/1482; A61B 18/1492; A61B 2018/0022; A61B 2018/00267;
(Continued)

(56) References Cited

U.S. PATENT DOCUMENTS 6,270,497 B1 8/2001 Sekino et al.
2011/0077648 A1 3/2011 Lee et al.
(Continued)

FOREIGN PATENT DOCUMENTS

JP H07-000351 A 1/1995
JP 2000-135222 A 5/2000
(Continued)

OTHER PUBLICATIONS

Office Action (Notice of Reasons for Refusal) issued on May 20, 2025, in corresponding Japanese Patent Application No. 2022-016303 and machine English translation of the Office Action. (6 pages).

*Primary Examiner* — Tigist S Demie
(74) *Attorney, Agent, or Firm* — .Buchanan Ingersoll & Rooney, PC

(57) ABSTRACT

A medical device and a medical system that can reduce supply of energy to an energy transmission element without performing an operation of pressing the energy transmission element against a biological tissue. The medical device includes an expandable body, a shaft portion connected to the expandable body, an energy transmission element provided in the expandable body, a housing connected to a proximal end portion of the shaft portion, a displacement shaft that compresses the expandable body in an axial direction, an operation knob that is capable of moving with respect to the housing, a detection unit that is housed in the housing and that detects compression of the expandable body caused by the displacement shaft, an electric wire that is capable of being connected to an electric power supply device for supplying electric power to the energy transmission element, and that extends to the energy transmission element.

20 Claims, 7 Drawing Sheets

(52) U.S. Cl.
CPC ............... *A61B 2018/00964* (2013.01); *A61B 2018/142* (2013.01); *A61B 2018/1465* (2013.01)

(58) Field of Classification Search
CPC .. A61B 2018/0038; A61B 2018/00577; A61B 2018/00595; A61B 2018/00702; A61B 2018/00964; A61B 2018/142; A61B 2018/1465
See application file for complete search history.

(56) References Cited

U.S. PATENT DOCUMENTS

| | | | | |
|---|---|---|---|---|
| 2012/0283713 | A1 | 11/2012 | Mihalik et al. | |
| 2016/0051321 | A1 | 2/2016 | Salahieh et al. | |
| 2021/0007791 | A1 | 1/2021 | Takahashi et al. | |
| 2021/0007800 | A1* | 1/2021 | Takahashi .......... | A61B 18/1492 |
| 2022/0211430 | A1* | 7/2022 | Takahashi .......... | A61B 18/1492 |
| 2022/0211431 | A1* | 7/2022 | Takahashi .......... | A61B 18/1492 |
| 2022/0211432 | A1* | 7/2022 | Takahashi .............. | A61B 17/11 |
| 2023/0404665 | A1* | 12/2023 | Takahashi .......... | A61B 18/1492 |

FOREIGN PATENT DOCUMENTS

| | | | |
|---|---|---|---|
| JP | 2011-072788 | A | 4/2011 |
| JP | 2016-010729 | A | 1/2016 |
| JP | 2019-513063 | A | 5/2019 |
| WO | 2017/172082 | A1 | 10/2017 |
| WO | 2019/189079 | A1 | 10/2019 |
| WO | 2020094094 | A1 | 5/2020 |
| WO | 2021/192914 | A1 | 9/2021 |

* cited by examiner

MEDICAL DEVICE AND MEDICAL SYSTEM

CROSS-REFERENCES TO RELATED APPLICATIONS

This application claims priority to Japanese Application No. 2022-016303 filed on Feb. 4, 2022, the entire content of which is incorporated herein by reference.

Technological Field

The present disclosure generally relates to a medical device and a medical system that include an expandable body in which an energy transmission element that is inserted into a living body and that cauterizes a biological tissue.

BACKGROUND DISCUSSION

Chronic heart failure is a known heart disease. Chronic heart failure is broadly classified into a systolic heart failure and a diastolic heart failure, based on a cardiac function index. In a patient suffering from the diastolic heart failure, a myocardium is hypertrophied and increases in stiffness (hardness). Therefore, blood pressure in a left atrium increases and the pumping function of a heart is decreased. Accordingly, the patient shows a heart failure symptom such as a pulmonary edema. There is also a heart disease in which a blood pressure on a right atrium side increases due to pulmonary hypertension or the like, the pumping function of a heart is decreased, and thus heart failure symptoms are shown.

In recent years, for the patients suffering from heart failure, attention has been paid to a shunt treatment in which a shunt (through-hole) serving as an escape route for an increased atrial pressure is formed in an atrial septum, which can reduce heart failure symptoms. In the shunt treatment, the atrial septum is accessed using a transvenous approach method, and a through-hole having a desired size is formed. Examples of a medical device for performing such a shunt treatment for an atrial septum include a medical device described in International Patent Application No. WO 2020/094094.

The medical device described in International Patent Application No. WO 2020/094094 includes two expandable bodies disposed at a distal end portion of an elongated shaft, an electrode disposed on the expandable bodies, and an operation unit disposed at a proximal end portion of the shaft and capable of sandwiching a biological tissue by the two expandable bodies. The electrode can supply electric power from an electric power supply device (console) that can be connected to the medical device. A surgeon can operate the operation unit to sandwich the biological tissue using the two expandable bodies, and cauterize the sandwiched biological tissue by supplying electric power to the electrode disposed on the expandable bodies.

When energy is supplied to the electrode without performing an operation of pressing the electrode serving as an energy transmission element against the biological tissue, there is a risk that a thrombus is formed by the electrode being exposed to blood, or that an unintended part is damaged by the electrode. However, by the medical device described in International Patent Application No. WO 2020/094094, it can be difficult to detect, by the electric power supply device, a state in which the electrode is pressed against the biological tissue.

SUMMARY

A medical device and a medical system are disclosed that can reduce a supply of energy to an energy transmission element without performing an operation of pressing an energy transmission element against a biological tissue.

A medical device is disclosed that includes: an expandable body that has a central axis and is configured to be expandable and contractible in a radial direction; an elongated shaft portion connected to the expandable body; an energy transmission element provided along the expandable body; a housing connected to a proximal end portion of the shaft portion; an elongated displacement shaft configured to be relatively displaced from an initial position to a compression position with respect to the shaft portion along an axial direction of the expandable body so as to compress the expandable body in the axial direction; an operation knob that is movable with respect to the housing; a detection unit housed in the housing and configured to detect compression of the expandable body caused by the displacement shaft; and an electric wire connectable to an electric power supply device that supplies electric power to the energy transmission element, and configured to pass through the housing and extend to the energy transmission element along the shaft portion. The expandable body includes: a concave portion recessed inward in the radial direction at an intermediate portion in the axial direction; a first connection portion connected to the shaft portion; and a second connection portion facing the first connection portion with the concave portion interposed between the second connection portion and the first connection portion in the axial direction. The displacement shaft extends from inside the housing along the shaft portion and is connected to the second connection portion of the expandable body. The concave portion includes, in order to define a receiving space capable of receiving a biological tissue, a distal erected section, a proximal erected section, and a bottom section located on an innermost side in the radial direction and disposed between the distal erected section and the proximal erected section. The distal erected section and the proximal erected section grip (or grasp) the biological tissue by the displacement of the displacement shaft from the initial position to the compression position. The energy transmission element is disposed along any one of the distal erected section and the proximal erected section in a manner of facing the receiving space. The operation knob includes: a knob body that protrudes from the housing, and that moves and operates the operation knob with respect to the housing; and an action portion movably disposed in the housing, and configured to act on the proximal end portion of the displacement shaft housed in the housing according to the movement and the operation of the operation knob and cause the displacement shaft to be displaced from the initial position to the compression position. The detection unit includes: a detection switch configured to switch a state according to the displacement of the displacement shaft form the initial position to the compression position caused by the operation knob; and an output unit configured to output a state change of the detection switch to the electric power supply device. The detection switch and the output unit are electrically independent from the electric wire.

In the medical device implemented as described above, the compression of the expandable body due to the movement of the displacement shaft from the initial position to the compression position when the operation knob is moved with respect to the housing can be detected by the detection unit, and can be output to the electric power supply device.

Therefore, since the electric power supply device can determine whether the operation knob is operated, it is possible to reduce the supply of the energy to the energy transmission element in a state in which the operation of pressing the energy transmission element against the biological tissue is not performed.

The medical device may further include a connection terminal capable of being connected to the electric power supply device, and a circuit board housed in the housing. The connection terminal may include a first terminal and a second terminal that are electrically independent from each other. The electric wire may include: a supply circuit capable of being connected to the electric power supply device via the first terminal and disposed on the circuit board; an electric wire main body configured to extend from the supply circuit to the energy transmission element along the shaft portion; and a connecting electric wire portion configured to extend from the supply circuit to the first terminal. The output unit may be capable of outputting the state change of the detection switch to the electric power supply device via the second terminal, and may include, on the circuit board, an output circuit electrically independent from the supply circuit. The detection switch may include a switch main body configured to change a state of the detection switch by being pressed, and a pressing portion configured to press the switch main body. The pressing portion may be displaceable between a pressing state in which the switch main body is pressed and a non-pressing state in which the switch main body is not pressed according to an operation of the operation knob for moving the displacement shaft from the initial position to the compression position. Accordingly, the operation of the operation knob is indirectly transmitted to the switch main body via the pressing portion. By integrating the supply circuit and the output circuit on one circuit board and integrating the first terminal and the second terminal into one connection terminal, wiring and soldering become easy. Further, by adopting a structure in which the pressing portion is disposed between the operation knob and the switch main body, it is no longer necessary to provide a positional limitation that the operation knob is disposed at a position where the operation knob can be brought into contact with the switch main body, and the degree of design freedom is improved. Therefore, it becomes relatively easy to implement a structure having a desired function in a limited space.

The action portion of the operation knob may include a contact portion disposed in the housing, the contact portion may be displaced between a non-contact position where the contact portion is not in contact with the pressing portion and a contact position where the contact portion is in contact with the pressing portion due to the operation of the operation knob for moving the displacement shaft from the initial position to the compression position, and the pressing portion may be brought into the pressing state by being brought into contact with the contact portion. Accordingly, it is possible to rather effectively shift the pressing portion from the non-pressing state to the pressing state using a position change of the contact portion according to the movement of the operation knob in the axial direction.

The action portion of the operation knob may be connected to the proximal end portion of the displacement shaft, and may be movable from a first position to a second position along the axial direction of the displacement shaft, and may move the displacement shaft from the initial position to the compression position according to the movement from the first position to the second position. Accordingly, it is possible to move the displacement shaft from the initial position to the compression position by the movement of the operation knob along the axial direction.

The first connection portion of the expandable body may be located at a proximal side with respect to the second connection portion. The displacement shaft may compress the expandable body in the axial direction by pulling the second connection portion in a proximal direction according to a movement from the initial position to the compression position located at the proximal side with respect to the initial position. The action portion of the operation knob may cause the displacement shaft to move from the initial position to the compression position according to a movement from the first position to the second position located at the proximal side with respect to the first position. Accordingly, by an operation of positioning the operation knob at the proximal side, the second connection portion disposed at a distal side with respect to the first connection portion of the expandable body can be pulled in the proximal direction via the displacement shaft, and the expandable body can be effectively compressed in the axial direction.

A medical system according to the disclosure includes the medical device and an electric power supply device. Accordingly, since the medical system can determine whether the operation knob is operated by the electric power supply device, it is possible to reduce the supply of the energy to the energy transmission element in the state in which the operation of pressing the energy transmission element against the biological tissue is not performed.

The electric power supply device may include: an input unit configured to receive the state change of the detection switch output from the output unit; an electric power output unit configured to output electric power to the energy transmission element via the electric wire; and a control unit configured to control output of the electric power from the electric power output unit. The electric power output unit may have an output mode in which electric power is capable of being output and a pause mode in which electric power is not capable of being output. The control unit may change the electric power output unit from the pause mode to the output mode when the state change of the detection switch corresponding to the compression of the expandable body is received by the input unit. Accordingly, the electric power supply device can determine whether the operation knob is operated based on information obtained from the output unit of the medical device, and can change the electric power output unit from the pause mode to the output mode. Since the energy can be supplied from the electric power supply device by the electric power output unit changing from the pause mode to the output mode, it is possible to reliably reduce the supply of the energy to the energy transmission element in the state in which the operation of pressing the energy transmission element against the biological tissue is not performed.

A medical device is disclosed comprising: an expandable body having a central axis and configured to be expandable and contractible in a radial direction; an elongated shaft portion configured to be connected to the expandable body; an energy transmission element provided along the expandable body; a housing configured to be connected to a proximal end portion of the shaft portion; an elongated displacement shaft configured to be relatively displaced from an initial position to a compression position with respect to the shaft portion along an axial direction of the expandable body and configured to compress the expandable body in the axial direction; an operation knob configured to be movable with respect to the housing; and a detection unit housed in the housing and configured to detect compression of the expandable body caused by the displacement shaft, the detection unit includes a detection switch configured to switch a state according to the displacement of the displacement shaft from the initial position to the compression position caused by the operation knob, and an output unit configured to output a state change of the detection switch to an electric power supply device.

An operation unit is disclosed for use in cauterization of a biological tissue, the operation unit comprising: a housing; an operation knob configured to be movable with respect to the housing; a detection unit housed in the housing configured to detect compression of an expandable body caused by a displacement shaft; an electric wire connectable to an electric power supply device configured to supply electric power to the energy transmission element, and configured to pass through the housing and extend to an energy transmission element along a shaft portion connected to the expandable body; the operation knob includes a knob body that protrudes from the housing and an action portion, the knob body configured to move and operate the operation knob with respect to the housing, the action portion configured to be movably disposed in the housing and configured to act on a proximal end portion of the displacement shaft housed in the housing according to the movement and the operation of the operation knob and to cause the displacement shaft to be displaced from the initial position to the compression position; and the detection unit includes a detection switch configured to switch a state according to the displacement of the displacement shaft from the initial position to the compression position caused by the operation knob, and an output unit configured to output a state change of the detection switch to the electric power supply device.

BRIEF DESCRIPTION OF THE DRAWINGS

FIG. 3A is a longitudinal sectional view, and FIG. 3B is a sectional view taken along a line A-A of FIG. 3A.

FIG. 4A is a longitudinal sectional view, and FIG. 4B is a sectional view taken along a line B-B of FIG. 4A.

FIG. 5A illustrates a plane where a terminal is present, and FIG. 5B illustrates a plane where a switch main body is present.

FIG. 6A illustrates a state in which a supply circuit of the switch mechanism is OFF, and FIG. 6B illustrates a state in which the supply circuit is ON.

FIG. 13A is a longitudinal sectional view before the operation knob is operated, and FIG. 13B is a longitudinal sectional view after the operation knob is operated.

FIG. 14A is a plan view before a biological tissue is gripped by an expandable body, and FIG. 14B is a plan view after the biological tissue is gripped by the expandable body.

DETAILED DESCRIPTION

Figure 1:
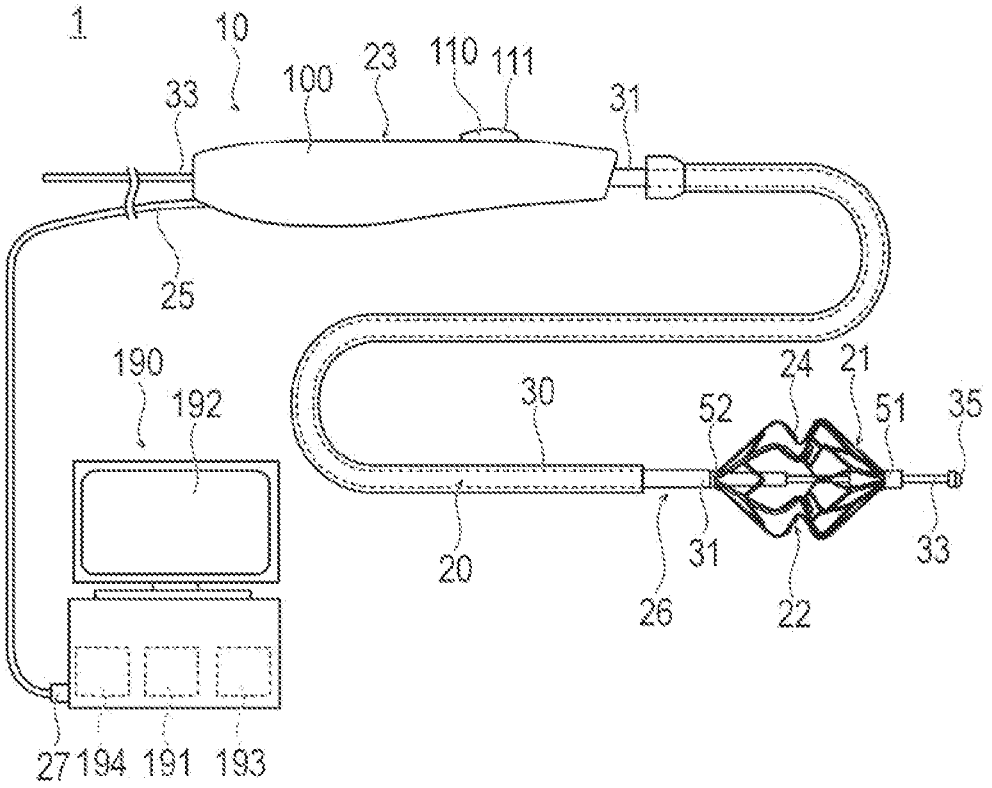
FIG. 1 is a side view illustrating an overall configuration of a medical system according to an embodiment.

Set forth below with reference to the accompanying drawings is a detailed description of embodiments of a medical device and a medical system that include an expandable body in which an energy transmission element that is inserted into a living body and that cauterizes a biological tissue. Note that since embodiments described below are preferred specific examples of the present disclosure, although various technically preferable limitations are given, the scope of the present disclosure is not limited to the embodiments unless otherwise specified in the following descriptions. In the drawings, the same or corresponding parts are denoted by the same reference numerals. In the description of the present embodiment, the description of the same or corresponding parts will be omitted or simplified as appropriate. For convenience of description, dimensional ratios in the drawings may be exaggerated and may be different from actual ratios. In addition, in the present description, a side where a medical device is inserted into a body lumen is referred to as a "distal side", and a side where the medical device is operated is referred to as a "proximal side". In the present description, the description "X to Y" indicating a range includes X and Y, and means "X or more and Y or less".

Figure 7:
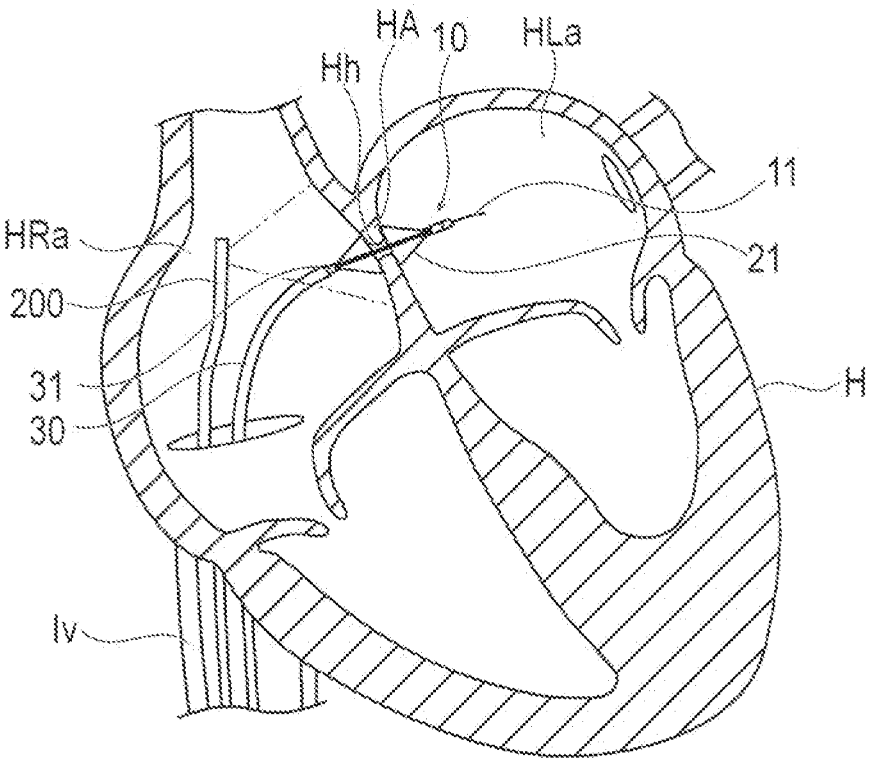
FIG. 7 is a schematic diagram schematically illustrating a state in which an expandable body is disposed in a through-hole of an atrial septum.

As illustrated in FIG. 7, a medical system 1 according to the present embodiment can perform a maintenance treatment of maintaining a size of a through-hole Hh that is formed in an atrial septum HA, which is a biological tissue of a heart H of a patient, and can be expanded by a balloon.

Figure 2:
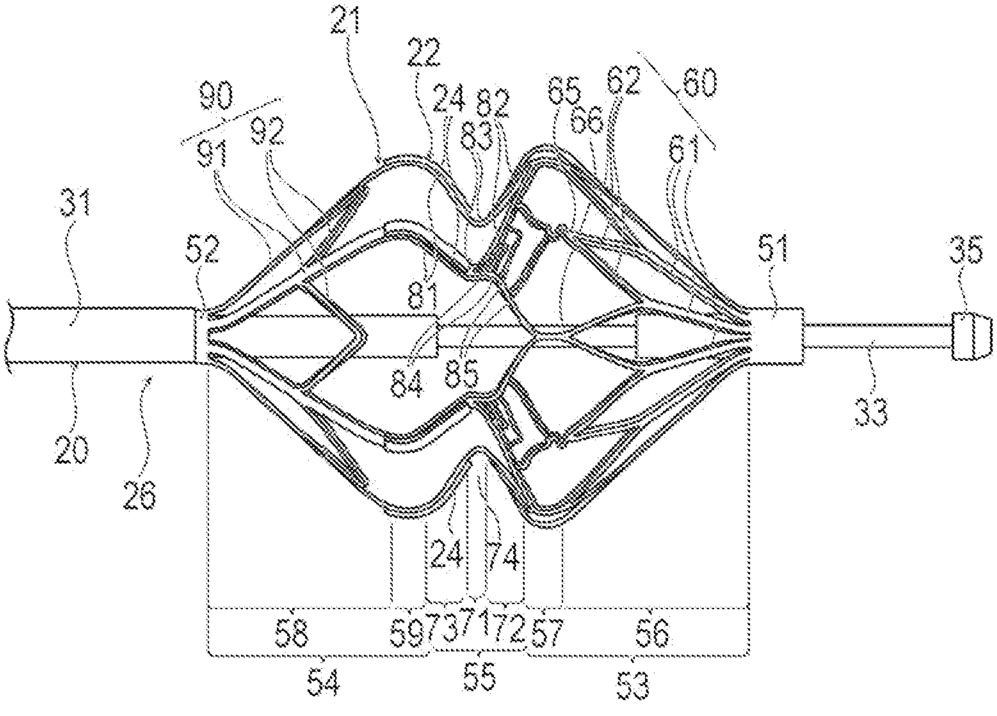
FIG. 2 is a side view illustrating a distal end portion of a medical device.

As illustrated in FIGS. 1 and 2, the medical system 1 according to the present embodiment includes a medical device 10 that is inserted into a living body and that cauterizes a biological tissue, and an electric power supply device 190 that supplies electric power to the medical device 10.

First, the medical device 10 will be described. The medical device 10 includes an elongated portion 20 that extends from a proximal end to a distal end, an expandable body 21 provided at a distal end portion of the elongated portion 20, an energy transmission element 22 provided with a plurality of electrodes 24 along the expandable body 21, an operation unit 23 connected to a proximal end portion of the elongated portion 20, a connection terminal 27 connectable to the electric power supply device 190, and a connection cable 25 extending from the operation unit 23 to the connection terminal 27.

The elongated portion 20 includes a shaft portion 31 that holds the expandable body 21 at the distal end portion, an outer tube 30 that houses the shaft portion 31, a displacement shaft 33, and a pulling portion 35 that is fixed to a distal end of the displacement shaft 33.

The shaft portion 31 is an elongated tube extending from the operation unit 23 to the expandable body 21. A proximal end portion of the shaft portion 31 is fixed to a distal end portion of the operation unit 23. A distal end portion of the shaft portion 31 is fixed to a proximal end portion of the expandable body 21.

The outer tube 30 is an elongated tube that covers the shaft portion 31, and is movable forward and backward in an axial direction (a direction of an axis of the elongated portion 20) with respect to the shaft portion 31. The expandable body 21 contracted in a radial direction can be housed in the outer tube 30 in a state in which the outer tube 30 moves to a distal side of the elongated portion 20. The radial direction is a direction orthogonal to an axis of the shaft portion 31. The surgeon can cause the expandable body 21 to be exposed (i.e., removed) from the outer tube 30 and to expand in the radial direction by moving the outer tube 30 in a state in which the expandable body 21 is housed toward the proximal side.

Figure 3A:
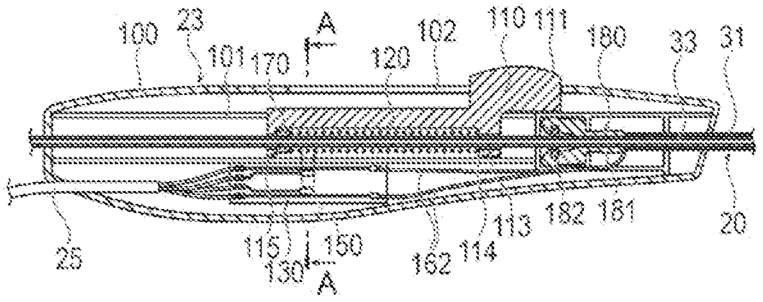
FIGS. 3A and 3B are diagrams illustrating an inside of an operation unit before an operation knob is operated.
Figure 3B:
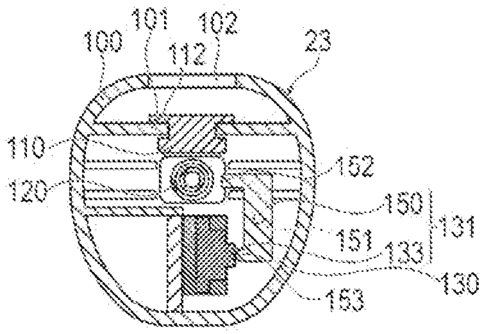

The displacement shaft 33 is an elongated tube disposed (or located) inside the shaft portion 31, and is movable forward and backward with respect to the shaft portion 31 in the axial direction. The displacement shaft 33 protrudes from a distal end of the shaft portion 31 toward the distal side, and protrudes from a distal end of the expandable body 21 toward the distal side. A distal end portion of the displacement shaft 33, which is located at the distal side with respect to the expandable body 21, is fixed to the pulling portion 35. A proximal end portion of the displacement shaft 33 extends from a proximal side of the operation unit 23 such that the proximal end portion of the displacement shaft 33 extends to a more proximal side of the medical device 10 than the operation unit 23. A guide wire lumen is formed along the axial direction inside the displacement shaft 33, and a guide wire 11 (see FIGS. 7 to 9) can be inserted through the guide wire lumen of the displacement shaft 33. The displacement shaft 33 can compress the expandable body 21 in the axial direction by being relatively displaced from an initial position (see FIGS. 3A and 3B) to a compression position (see FIGS. 4A and 4B) with respect to a shaft portion 21 along an axial direction of the expandable body 21.

The pulling portion 35 can be an annular member fixed to an outer peripheral surface of the distal end portion of the displacement shaft 33, and protrudes outward in the radial direction from the outer peripheral surface of the displacement shaft 33. The pulling portion 35 is not fixed to the expandable body 21. An outer diameter of the pulling portion 35 is larger than an inner diameter of the distal end portion of the expandable body 21. Therefore, the pulling portion 35 can abut on the distal end portion of the expandable body 21 from the distal side, pull the expandable body 21 toward a proximal direction, and apply a compressive force, which compresses along an axial direction of the shaft portion 31, to the expandable body 21.

As illustrated in FIGS. 1, 3A, 3B, 4A, and 4B, the operation unit 23 includes a housing 100 that can be gripped by the surgeon, an operation knob 110 that is allowed to be moved along the axial direction by the surgeon, an elastic body 120 that transmits the movement of the operation knob 110 to the displacement shaft 33, a detection unit 130 that detects compression of the expandable body 21, an electric wire 160 that transmits electric power from the electric power supply device 190 to the electrodes 24, and a shaft connecting portion 180 that connects the shaft portion 31 to the housing 100.

The housing 100 can include a guide rail 101 that holds the operation knob 110 in a manner of being linearly slidable toward the axial direction, and an opening 102 that causes a part of the operation knob 110 to be exposed outside of the housing 100.

The operation knob 110 is slidable with respect to the housing 100 along the axial direction of the shaft portion 31. The operation knob 110 can cause the displacement shaft 33 to move from the initial position (see FIGS. 3A and 3B) to the compression position (see FIGS. 4A and 4B). The operation knob 110 includes a knob body 111 that is exposed outside from the opening 102 of the housing 100 so that the surgeon can operate the knob body, a sliding portion 112 that comes into contact with the guide rail 101 in a manner of being linearly slidable toward the axial direction inside the housing 100, and a contact portion 113 that can come into contact with a pressing portion 150. The operation knob 110 further includes an action portion 114 that can abut on a distal end of the elastic body 120 from the distal side, and a stopper 115 that can abut on a proximal surface of a ring-shaped fixing member 170 fixed to the displacement shaft 33. The contact portion 113 is provided only in a part of the operation knob 110 in the axial direction. In the present embodiment, the contact portion 113 is formed on an outer peripheral surface of a part surrounding the displacement shaft 33 in the vicinity of the action portion 114. The contact portion 113 can be displaced from a non-contact position where the contact portion 113 is not in contact with the pressing portion 150 to a contact position where the contact portion 113 is in contact with the pressing portion 150 by an operation of the operation knob 110 for moving the displacement shaft 33 from the initial position to the compression position. The contact portion 113 moves from the non-contact position to the contact position, so that the contact portion 113 can abut on the pressing portion 150 and can press the pressing portion 150. The action portion 114 is a portion that causes a pulling force toward the proximal direction to act on the displacement shaft 33 via the elastic body 120. The action portion 114 is connected to the proximal end portion of the displacement shaft 33 via the elastic body 120, and is movable from a first position to a second position along an axial direction of the displacement shaft 33. The action portion 114 can cause the displacement shaft 33 to move from the initial position to the compression position according to the movement from the first position to the second position. The stopper 115 is disposed at the proximal side with respect to the action portion 114. The stopper 115 abuts on the proximal surface of the fixing member 170 fixed to the displacement shaft 33, thereby limiting the displacement shaft 33 from moving more than necessary toward the proximal direction with respect to the operation knob 110.

As illustrated in FIGS. 3A, 3B, 4A, and 4B, the elastic body 120 is disposed between the operation knob 110 and the displacement shaft 33 in order to adjust a pulling force transmitted from the operation knob 110 to the displacement shaft 33. The elastic body 120 can be a coil spring surrounding the displacement shaft 33. The elastic body 120 can elastically expand and contract along the axial direction of the displacement shaft 33. The distal end of the elastic body 120 can abut on the proximal surface of the action portion 114 of the operation knob 110. A proximal end of the elastic body 120 can abut on a distal surface of the fixing member 170 fixed to the displacement shaft 33.

As illustrated in FIGS. 3A, 3B, 4A, 4B, 5A, 5B, 6A, and 6B, the detection unit 130 includes a detection switch 131 that switches a state according to the displacement of the displacement shaft 33 caused by the operation knob 110, and an output unit 132 that outputs a state change (i.e., a change of ON/OFF) of the detection switch 131 to the electric power supply device 190. The detection switch 131 and the output unit 132 are electrically independent from the electric wire 160.

The state of the detection switch 131 is switched according to the displacement of the displacement shaft 33 from the initial position (see FIGS. 3A and 3B) to the compression position (see FIGS. 4A and 4B) caused by the operation knob 110. The detection switch 131 includes the pressing portion 150 that moves according to the displacement of the operation knob 110, and a switch main body 133 that can be pushed by the pressing portion 150.

Figure 4A:
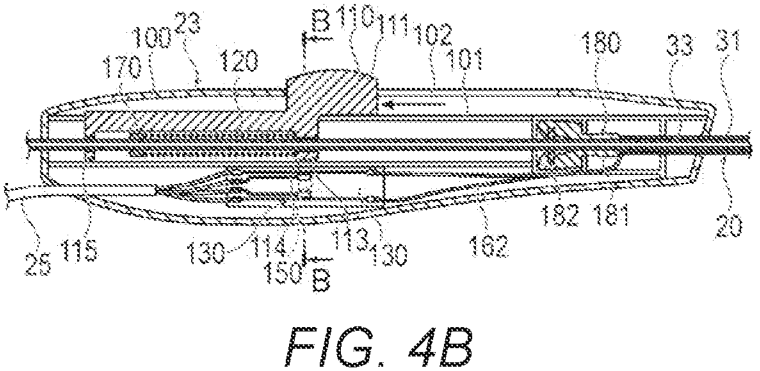
FIGS. 4A and 4B are diagrams illustrating the inside of the operation unit after the operation knob is operated.
Figure 4B:
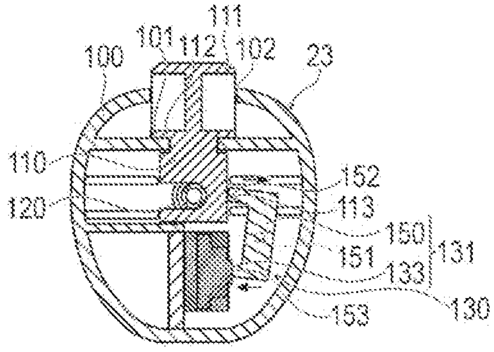
Figure 5A:
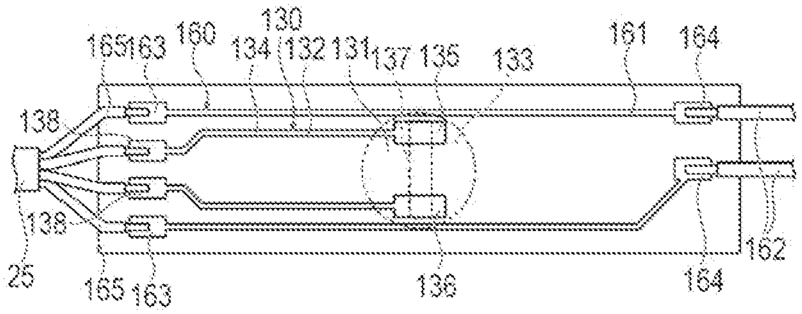
FIGS. 5A and 5B are plan views illustrating a switch mechanism of the medical device.
Figure 5B:
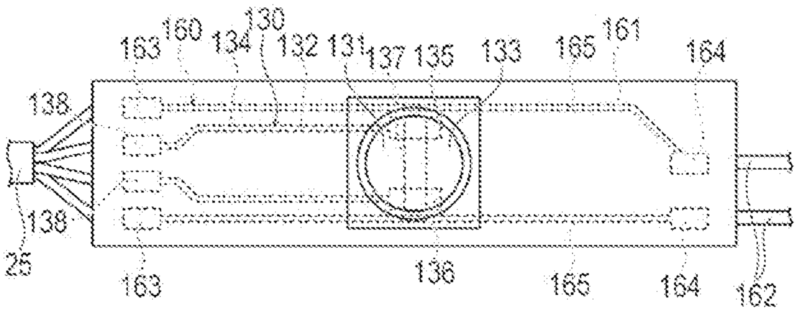

The pressing portion 150 includes a rotation shaft 151 rotatably connected to the housing 100, a press input portion 152 capable of coming into contact with the contact portion 113 of the operation knob 110, and a press output portion 153 capable of coming into contact with the switch main body 133 of the detection switch 131. The rotation shaft 151 is rotatable about an axis parallel to a central axis of the displacement shaft 33. The press input portion 152 is disposed at the compression position where the press input portion 152 can come into contact with the contact portion 113, as illustrated in FIGS. 4A and 4B, when the operation knob 110 moves from the initial position illustrated in FIGS. 3A and 3B toward the proximal side along the axial direction. The press input portion 152 moves by being pressed (i.e., contacted) by the contact portion 113, and rotates the pressing portion 150. When the pressing portion 150 is rotated by the contact portion 113 being pressed (i.e., contacted) by the press input portion 152, the press output portion 153 can push (i.e., contact) the switch main body 133. That is, the pressing portion 150 can be displaced between a pressing state in which the switch main body 133 is pressed and a non-pressing state in which the switch main body 133 as described later is not pressed, according to the operation of the operation knob 110 for moving the displacement shaft 33 from the initial position to the compression position.

The switch main body 133 is biased by a force generated by a spring in a state in which an external force does not act on the switch main body 133. By being pressed by the press output portion 153 of the pressing portion 150 to contract the spring, the switch main body 133 is pushed.

As illustrated in FIGS. 5A, 5B, 6A, and 6B, the output unit 132 outputs the state change of the detection switch 131 to the electric power supply device 190 via a cable 25. The output unit 132 can include, on a circuit board, an output circuit 134 electrically independent from a supply circuit 161 that supplies electric power to the electrodes 24. The output circuit 134 can include a first fixed contact 135 and a second fixed contact 136 that are disposed apart from each other on the circuit board, a movable contact 137 that is pushed down by the switch main body 133 and that is capable of coming into contact with both the first fixed contact 135 and the second fixed contact 136, and two state output terminals 138 that are electrically connected to the first fixed contact 135 and the second fixed contact 136, respectively. Both the first fixed contact 135 and the second fixed contact 136 can be connected to the electric power supply device 190 by second terminals 139 disposed on the connection terminal 27 from any one of the two state output terminals 138 via the connection cable 25.

The movable contact 137 is usually separated from the first fixed contact 135 and second fixed contact 136, and when the switch main body 133 is pushed, the movable contact 137 moves accordingly, and comes into contact with both the first fixed contact 135 and the second fixed contact 136. Accordingly, the first fixed contact 135 and the second fixed contact 136 are electrically connected via the movable contact 137.

The electric wire 160 can include the supply circuit 161 disposed on the circuit board, electric wire main bodies 162 extending from the supply circuit 161 to the energy transmission element 22 along the shaft portion 31, and connecting electric wire portions 165 extending from the supply circuit 161 to first terminals 166 disposed at the connection terminal 27. The supply circuit 161 includes two energy input terminals 163 connected to the connecting electric wire portions 165, and two energy output terminals 164 connected to the electric wire main bodies 162.

The two energy input terminals 163 can be connected to the electric power supply device 190 via the connection cable 25 and the connection terminal 27.

The two energy output terminals 164 can be electrically connected to each of an electrode pair of the energy transmission element 22, which is bipolar, respectively, via the electric wire main bodies 162 extending from the detection switch 131 to the energy transmission element 22 along the shaft portion 31.

As described above, the connection terminal 27 that can be connected to the electric power supply device 190 can include the first terminals 166 that are electrically connected to the supply circuit 161, and the second terminals 139 that are electrically connected to the output circuit 134. The connection terminal 27 may be not only directly connected to the electric power supply device 190, but also may be indirectly connected to the electric power supply device 190 via another extension cable or the like.

As illustrated in FIGS. 3A, 3B, 4A, and 4B, the shaft connecting portion 180 includes a holding portion 181 that is fixed and held inside the housing 100, and a seal member 182 that is disposed inside the holding portion 181. The holding portion 181 is a substantially cylindrical member that is connected in close contact with a proximal end of the shaft portion 31. The seal member 182 is an annular member that is disposed inside the holding portion 181 at the proximal side with respect to the shaft portion 31 and that is slidably in contact with the outer peripheral surface of the displacement shaft 33. The seal member 182 helps prevent blood or the like from flowing into the housing 100 from between the shaft portion 31 and the displacement shaft 33.

As illustrated in FIGS. 1 and 2, the expandable body 21 can include a force receiving portion 51 disposed at the distal end of the expandable body 21, a proximal end connection portion 52 disposed at the proximal end of the expandable body 21, a second connection portion 53 connected to the force receiving portion 51, a first connection portion 54 connected to the proximal end connection portion 52, and concave portions 55 formed between the second connection portion 53 and the first connection portion 54.

The force receiving portion 51 can be annular, and can receive a force from the pulling portion 35 disposed on the distal side toward the proximal direction. The proximal end connection portion 52 can be annular, and is fixed to the distal end portion of the shaft portion 31.

The second connection portion 53 can be deformable in a flexible manner. The second connection portion 53 can include a distal extension portion 56 extending outward in the radial direction from the force receiving portion 51 toward the proximal direction, and a distal apex portion 57 disposed on a proximal side of the distal extension portion 56 and curved outward in a protrusive manner in the radial direction.

The second connection portion 53 includes a plurality of distal strut structures 60 extending outward in the radial direction from the force receiving portion 51 toward the proximal direction to form the distal extension portion 56. The plurality of distal strut structures 60 can be arranged at substantially equal intervals in a circumferential direction of the expandable body 21 at the time of expansion.

Each of the distal strut structures 60 can include a first strut 61 extending from the force receiving portion 51 toward the proximal direction, and a second strut 62 extending from a proximal end of the first strut 61 toward the proximal direction and connected to the distal apex portion 57.

Each of the first struts 61 extends from the force receiving portion 51 substantially parallel to an axis of the expandable body 21 when viewed from the outside in the radial direction. Each of the second struts 62 branches into two branches in a manner of extending toward the circumferential direction of the expandable body 21 while going from the proximal end of each of the first struts 61 toward the proximal direction, and joins at a first junction portion 65 or a second junction portion 66. The first junction portions 65 and the second junction portions 66 are alternately arranged at substantially equal intervals in the circumferential direction of the expandable body 21 at the time of expansion.

Each of the first junction portions 65 is connected to the distal apex portion 57 disposed in the same phase as the electrodes 24 in the circumferential direction of the expandable body 21. Each of the second junction portions 66 is connected to the distal apex portion 57 disposed in different phases with respect to the electrodes 24 in the circumferential direction of the expandable body 21.

The first connection portion 54 is deformable in a flexible manner. The first connection portion 54 includes a proximal extension portion 58 extending outward in the radial direction from the proximal end connection portion 52 toward a distal direction, and a proximal apex portion 59 disposed on a distal side of the proximal extension portion 58 and curved outward in a protrusive manner in the radial direction.

The proximal extension portion 58 includes a plurality of proximal strut structures 90. The proximal strut structures 90 can be disposed in the same phase as a plurality of electrode disposing portions 81 in the circumferential direction of the expandable body 21. Each of the proximal strut structures 90 can include a plurality of third struts 91 extending, substantially parallel to the axis of the expandable body 21 when viewed from the outside in the radial direction, from the distal end portion of the shaft portion 31 to the proximal apex portion 59, and a plurality of secondary struts 92 connecting the third struts 91 adjacent to each other in the circumferential direction. Each of the secondary struts 92 is connected to the two third struts 91 adjacent to each other in the circumferential direction. The secondary struts 92 can be bent. Therefore, even in a case in which a distance between the two third struts 91 adjacent to each other when the expandable body 21 is expanded becomes long, the two third struts 91 can be continuously supported while the secondary struts 92 are deformed into a shape close to a straight line. Therefore, the expandable body 21 can expand while extending the third struts 91 at substantially equal intervals by a compressive force applied by the displacement shaft 33.

The concave portions 55 are deformable in a flexible manner. When the expandable body 21 is expanded, the concave portions 55 are recessed inward in the radial direction, and extend to connect the proximal apex portion 59 and the distal apex portion 57. The concave portions 55 define a receiving space 74 capable of receiving a biological tissue of a living body when the expandable body 21 is expanded.

Each of the concave portions 55 includes a bottom section 71 located on the innermost side in the radial direction, a distal erected section 72 extending outward in the radial direction from a distal end of the bottom section 71 to the distal apex portion 57, and a proximal erected section 73 extending outward in the radial direction from a proximal end of the bottom section 71 to the proximal apex portion 59.

It is preferable that intervals between the proximal erected sections 73 and the distal erected sections 72 are slightly larger on the outside than those on the inside of the radial direction in the axial direction at the time of expansion of the expansion portion. Accordingly, it is relatively easy to dispose the biological tissue from the outside in the radial direction between the proximal erected sections 73 and the distal erected sections 72.

The concave portions 55 have a plurality of concave strut structures 80 arranged in the circumferential direction. Each of the plurality of concave strut structures 80 can include the electrode disposing portions 81 disposed on the proximal erected sections 73 and a plurality of facing portions 82 disposed on the distal erected sections 72, and further includes a plurality of bottom section connecting portions 83 each connecting one of the electrode disposing portions 81 and one of the facing portions 82, which constitute a pair, to the bottom sections 71.

The electrode disposing portions 81 are arranged at substantially equal intervals in the circumferential direction of the expandable body 21. The facing portions 82 are arranged at substantially equal intervals in the circumferential direction of the expandable body 21. The plurality of bottom section connecting portions 83 are arranged at substantially equal intervals in the circumferential direction of the expandable body 21.

The facing portions 82 each face a respective one of the electrodes 24 at the time of expansion of the expandable body 21. Each of the facing portions 82 includes a plurality of distal erected struts 84 that branch into two branches while spreading toward the distal direction in a manner of extending substantially along the circumferential direction of the expandable body 21 from distal ends of the bottom section connecting portions 83, and a plurality of back contact portions 85. The plurality of back contact portions 85 connect the two distal erected struts 84 branched from each of the bottom section connecting portions 83. The back contact portions 85 are arranged side by side from a side close to the bottom sections 71 to a side close to the distal apex portion 57. Each of the back contact portions 85 is curved such that a part between both ends connected to the two distal erected struts 84 protrudes toward the distal apex portion 57. Each of the back contact portions 85 is more likely to bend on the side close to the distal apex portion 57 with both the ends connected to the distal erected struts 84 as supporting points. Therefore, the back contact portions 85 can be bent by a force toward the distal side. The force is received from the electrodes 24 disposed on the proximal erected sections 73. Therefore, the biological tissue sandwiched between the electrodes 24 and the back contact portions 85 can be brought into close contact with the electrodes 24. Of the back contact portions 85 forming the facing portions 82, the back contact portion 85 closest to the distal apex portion 57 is connected to the distal apex portion 57 at a part protruding toward the distal apex portion 57. The number of the back contact portions 85 forming the facing portions 82 is not particularly limited.

The energy transmission element 22 includes the plurality of electrodes 24. Each of the electrodes 24 is disposed on a surface of a respective one of the electrode disposing portions 81 that forms an inner side of the concave portion 55. The electrodes 24 are disposed in relatively close contact with the surfaces of the electrode disposing portions 81 that form the inner side of the concave portions 55. A surface of at least a part of the electrodes 24, which faces the receiving space 74 At the time of expansion, has a convex curved surface shape. The surface of the electrodes 24 that faces the receiving space 74 at the time of expansion may have a planar shape.

The electrodes 24 are disposed on surfaces facing a distal side of the proximal erected sections 73 at the time of expansion of the expandable body 21. Since the electrodes 24 are provided on the proximal erected sections 73, when the concave portions 55 hold the atrial septum HA, energy from the electrodes 24 is transmitted from a right atrium side to the atrial septum HA. When the electrodes 24 are provided on the distal erected sections 72, the energy from the electrodes 24 is transmitted from a left atrium side to the atrial septum HA.

The electrodes 24 can be implemented by, for example, bipolar electrodes that receive electric power from the electric power supply device 190. In the case of the electrodes 24 being bipolar electrodes, energization is performed between the electrodes 24 disposed in the electrode disposing portions 81.

Further, the electrodes 24 may be implemented as monopolar electrodes. In the case of the electrodes 24 being monopolar electrodes, energization is performed with a counter electrode plate prepared outside a body. In addition, the electrodes 24 may be heating elements (electrode tips) that receives high-frequency electric energy from an energy supply apparatus and that generates heat.

In the present embodiment, the electrodes 24 are provided on the proximal erected sections 73 and the back contact portions 85 are provided on the distal erected sections 72. Alternatively, the electrodes 24 may be provided on the distal erected sections 72 and the back contact portions 85 may be provided on the proximal erected sections 73.

In the present embodiment, the operation knob 110, the elastic body 120, the displacement shaft 33, and the pulling portion 35 which are capable of moving the distal end of the expandable body 21, and the housing 100 and the shaft portion 31 which are capable of moving the proximal end of the expandable body 21 function as a displacement mechanism 26 that compresses the expandable body 21 in the axial direction by relatively displacing the proximal end of the expandable body 21 with respect to the distal end of the expandable body 21 substantially along the central axis.

The expandable body 21 can be, for example, cut out from a cylinder and integrally formed. The struts that form the expandable body 21 may have, for example, a thickness of 50 μm to 500 μm and a width of 0.3 mm to 2.0 mm. Alternatively, the struts that form the expandable body 21 may have a dimension out of the range of the thickness being 50 μm to 500 μm and the width being 0.3 mm to 2.0 mm. The shape of the struts is not particularly limited, and may have, for example, a circular cross-sectional shape or a cross-sectional shape other than the circular cross-sectional shape.

The expandable body 21 can be formed of or fabricated from a metal material. As the metal material of the expandable body 21, for example, a titanium-based alloy (Ti—Ni, Ti—Pd, Ti—Nb—Sn or the like), a copper-based alloy, stainless steel, β titanium steel, and a Co—Cr alloy can be used. In accordance with an embodiment, it can be more preferable to use an alloy or the like having a spring property, such as a nickel titanium alloy as the metal material for the expandable body 21. However, a material for a wire member of the expandable body 21 is not limited to a metal material, and may be formed of other materials.

In accordance with an embodiment, it is more preferable that the outer tube 30 and the shaft portion 31 of the elongated portion 20 are formed of or fabricated from a material having a certain degree of flexibility. Examples of such a material having a certain degree of flexibility for the outer tube 30 and the shaft portion 31 of the elongated 20 can include polyolefins such as polyethylene, polypropylene, polybutene, ethylene-propylene copolymer, ethylene-vinyl acetate copolymer, ionomer, and a mixture of two or more thereof, fluororesins such as a soft polyvinyl chloride resin, polyamide, polyamide elastomer, polyester, polyester elastomer, polyurethane, and polytetrafluoroethylene, polyimide, PEEK, silicone rubber, and latex rubber.

The displacement shaft 33 and the pulling portion 35 can be formed of or fabricated from, for example, an elongated wire including a superelastic alloy such as a nickel-titanium alloy or a copper-zinc alloy, a metal material such as stainless steel, or a resin material having a relatively high rigidity. In addition, the displacement shaft 33 and the pulling portion 35 may be formed by coating the above material with polyvinyl chloride, polyethylene, polypropylene, ethylene-propylene copolymer, or a resin material such as fluororesin.

Next, the electric power supply device 190 will be described. As illustrated in FIG. 1, the electric power supply device 190 can include an electric power output unit 191, a notification unit 192, a control unit 193, and an input unit 194.

The electric power output unit 191 is a unit that outputs electric power for performing a maintenance treatment to the first terminals 166 of the medical device 10. The electric power output unit 191 is controlled by the control unit 193, and can output a high-frequency current for any period of time with any electric power. The electric power output unit 191 has an output mode in which electric power can be output and a pause mode in which electric power cannot be output. Only when the electric power output unit 191 is in the output mode, can the surgeon perform an operation to start cauterization.

The input unit 194 is a unit to which information on the state change of the detection switch 131 output from the output unit 132 of the medical device 10 is received from the second terminals 139.

The notification unit 192 is a unit that notifies the surgeon of a situation of control, a warning, or the like. The notification unit 192 can be, for example, a speaker that gives a notification with a sound or an image monitor that gives a notification with an image. A display method of the image monitor and an output method using the speaker are not particularly limited. The notification unit 192 may be an external device that is not implemented in the electric power supply device 190 and that is communicably connected to the electric power supply device 190.

The control unit 193 can include a central processing unit (CPU), a storage circuit, and an operation program. An interface such as a keyboard or a mouse may be connected to the control unit 193. The control unit 193 can be, for example, a computer.

The control unit 193 can control the electric power output unit 191 to control the output of the high-frequency current from the electric power output unit 191. The control unit 193 can cause the electric power output unit 191 to output any electric power for any period of time. Therefore, when the input unit 194 receives the state change of the detection switch 131 corresponding to the compression of the expandable body 21, the control unit 193 can cause the electric power output unit 191 to change from the pause mode to the output mode. The control unit 193 can cause the notification unit 192 to provide information indicating which mode the electric power output unit 191 is in and whether the mode of the electric power output unit 191 has changed.

Figure 12:
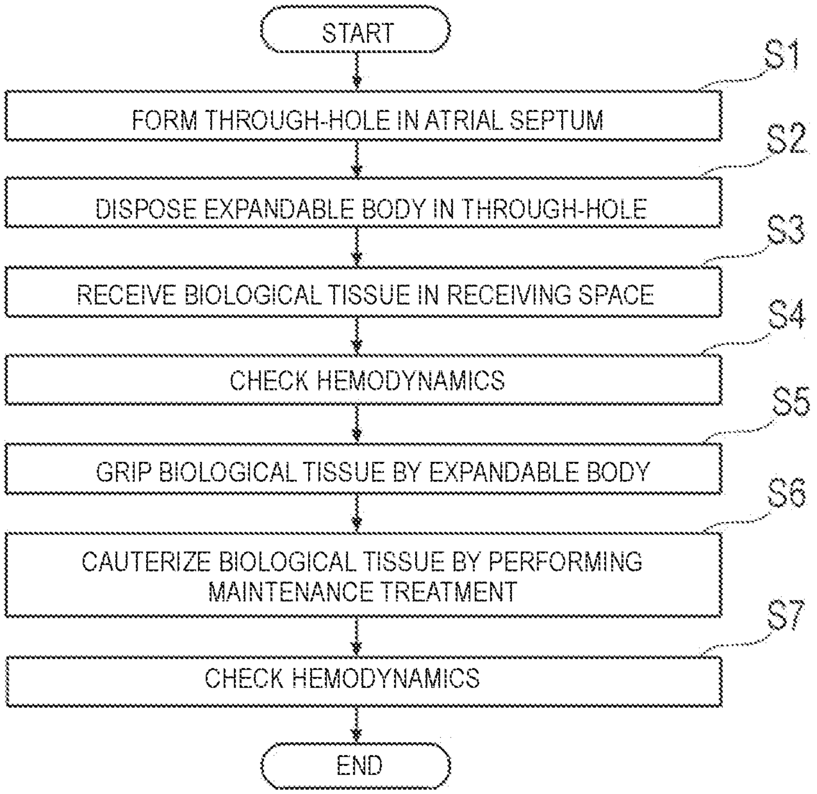
FIG. 12 is a flowchart illustrating a method for using a medical system in accordance with an embodiment of the disclosure.

Next, a method for using the medical device 10 according to the present embodiment will be described with reference to a flowchart illustrated in FIG. 12. The method is performed on a patient suffering from a heart failure (left heart failure). More specifically, as illustrated in FIGS. 4A and 4B, the method is a treatment method that is performed on a patient suffering from a chronic heart failure in which a myocardium of a left ventricle of the heart H is hypertrophied and increases in stiffness (hardness), resulting in an increase in blood pressure in a left atrium Hla.

The method for using the medical device 10 according to the present embodiment includes forming the through-hole Hh in the atrial septum HA (S1), disposing the expandable body 21 in the through-hole Hh (S2), receiving the biological tissue in the receiving space 74 (S3), checking hemodynamics in the vicinity of the through-hole Hh (S4), gripping the through-hole Hh by the expandable body 21 (S5), performing the maintenance treatment for maintaining the size of the through-hole Hh (S6), and checking the hemodynamics in the vicinity of the through-hole Hh after the maintenance treatment is performed (S7).

When the surgeon forms the through-hole Hh, the surgeon delivers an introducer, in which a guiding sheath and a dilator are combined together, to the vicinity of the atrial septum HA. The introducer can be delivered to, for example, a right atrium Hra via an inferior vena cava Iv. In addition, the introducer can be delivered using the guide wire 11. The surgeon can insert the guide wire 11 into the dilator, and deliver the introducer along the guide wire 11. The insertion of the introducer into a living body or the insertion of the guide wire 11 into a living body can be performed using a known method such as using an introducer for blood vessel introduction.

In S1, the surgeon causes a puncture device to penetrate through the atrial septum HA from a right atrium Hra side toward a left atrium Hla side to form the through-hole Hh in a fossa ovalis of the atrial septum HA. As the puncture device, for example, a device such as a wire having a sharp distal end can be used. The puncture device is inserted into the dilator, and is delivered to the atrial septum HA. After the guide wire 11 is removed from the dilator, instead of the guide wire 11, the puncture device can be delivered to the atrial septum HA.

Figure 8:
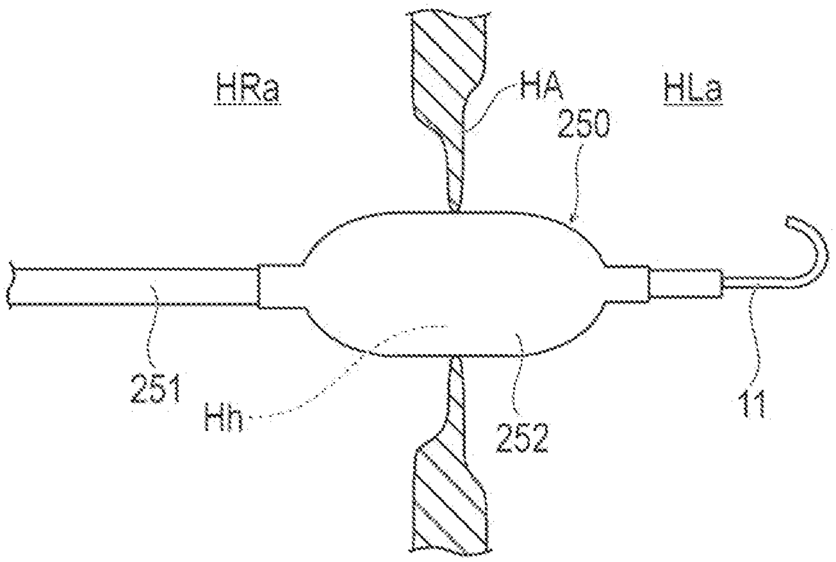
FIG. 8 is a sectional view illustrating a state in which a balloon is inserted into the atrial septum.

Next, the surgeon delivers a balloon catheter 250 to the vicinity of the atrial septum HA along the guide wire 11 inserted in advance. As illustrated in FIG. 8, the balloon catheter 250 has a balloon 252 at a distal end portion of a shaft portion 251. When the balloon 252 is disposed in the atrial septum HA, the balloon 252 is inflated in the radial direction, and the through-hole Hh is pressed to be spread or widen.

Figure 9:
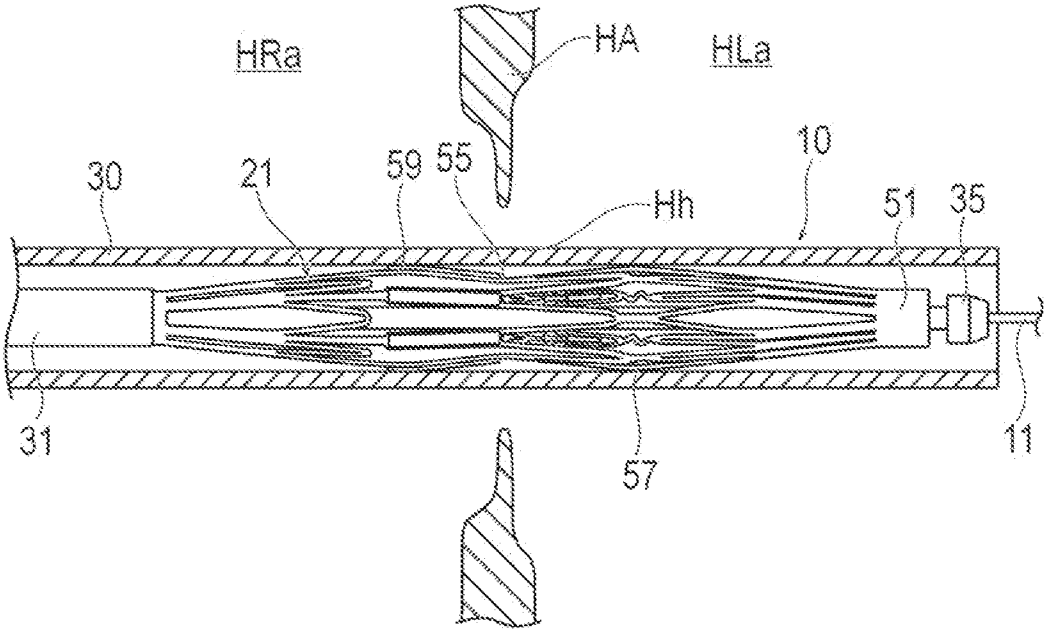
FIG. 9 is a sectional view illustrating a state in which the distal end portion of the medical device is inserted into the atrial septum.

In S2, as illustrated in FIG. 9, the medical device 10 is delivered to the vicinity of the atrial septum HA along the guide wire 11 inserted in advance. At this time, the distal end portion of the medical device 10 penetrates through the atrial septum HA and reaches the left atrium Hla. When the medical device 10 is inserted, the expandable body 21 is housed in the outer tube 30. The medical device 10 may be a device without the outer tube 30. In this case, a sheath corresponding to the outer tube 30 is separately prepared, and in S2, the sheath is delivered to the vicinity of the atrial septum HA along the guide wire 11 in advance so that a distal end portion of the sheath reaches the left atrium Hla via the through-hole Hh of the atrial septum HA. Next, the expandable body 21 of the medical device 10 is inserted into the sheath from a proximal end of the sheath, and as in FIG. 9, the distal end portion of the expandable body 21 is delivered to the left atrium Hla via the through-hole Hh of the atrial septum HA.

Figure 10:
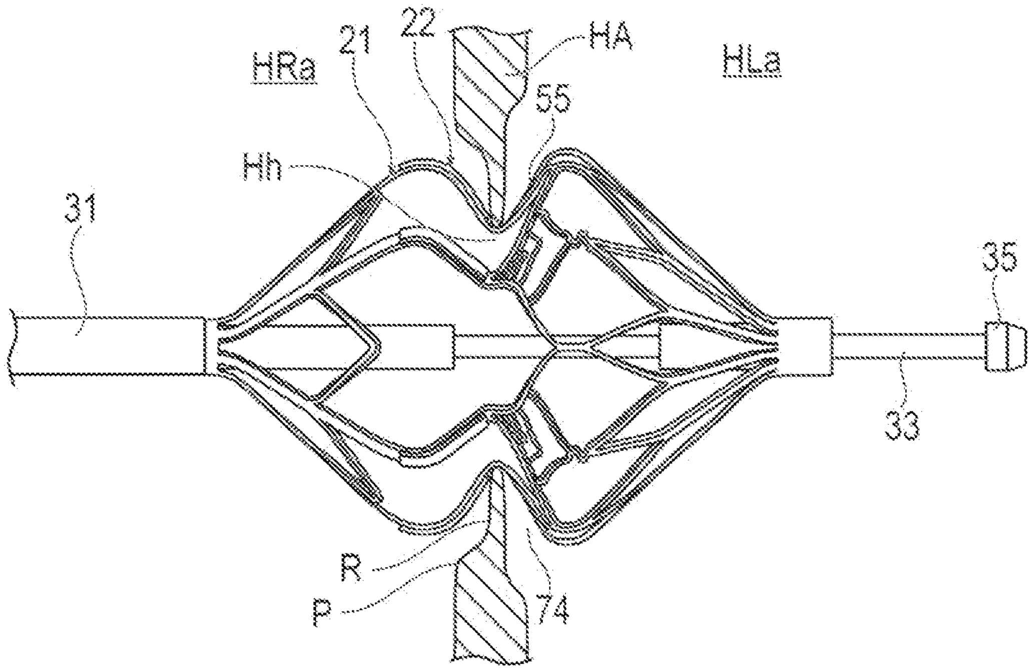
FIG. 10 is a sectional view illustrating a state in which the expandable body is disposed in the atrial septum.

Next, in S3, the expandable body 21 is exposed by moving the outer tube 30 toward the proximal side. Accordingly, as illustrated in FIG. 10, the expandable body 21 is expanded in diameter, the concave portions 55 are disposed in the through-hole Hh of the atrial septum HA, and the biological tissue surrounding the through-hole Hh is received in the receiving space 74. In S1, when the through-hole Hh is pressed to be spread by the balloon 252, the through-hole Hh may not be equally pressed to be spread toward the radial direction and may have a slit shape. In this case, when the expandable body 21 is expanded in diameter and the biological tissue surrounding the through-hole Hh is received in the receiving space 74, the expandable body 21 has a shape in which the through-hole Hh expands in a direction different from a direction in which a slit extends.

When the biological tissue surrounding the through-hole Hh is received in the receiving space 74, the hemodynamics is checked in S4. As illustrated in FIG. 7, the surgeon delivers a hemodynamics checking device 200 to the right atrium Hra via the inferior vena cava Iv. As the hemodynamics checking device 200, for example, a known echo catheter can be used. The surgeon can cause a display device such as a display to display an echo image acquired by the hemodynamics checking device 200, and check the amount of blood passing through the through-hole Hh based on a display result. At this time, when the amount of the blood passing through the through-hole Hh does not reach a desired amount, the surgeon moves the outer tube 30 to the distal side to house the expandable body 21 in the outer tube 30, and then removes the expandable body 21 from the through-hole Hh together with the outer tube 30. Next, a balloon catheter including a balloon having an expanded diameter larger than that of the balloon 252 used in S1 is used and the through-hole Hh is pressed to be spread again, and the process returns to S2.

Figure 11:
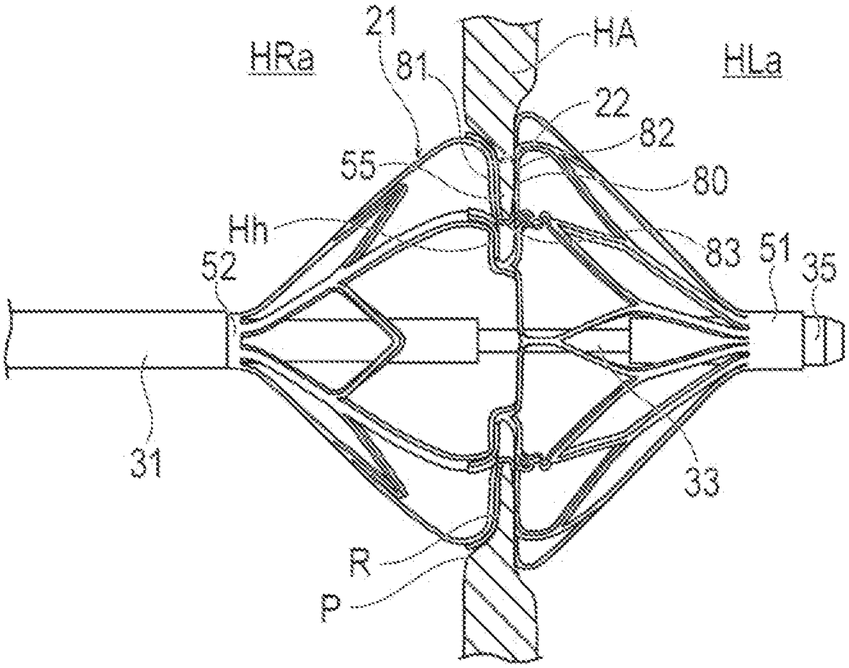
FIG. 11 is a sectional view illustrating a state in which an energy transmission element disposed in a concave portion of the expandable body is brought into close contact with a biological tissue.

In S5, the surgeon operates the operation unit 23 in a state in which the atrial septum HA is received in the receiving space 74 of the concave portions 55, and moves the knob body 111 toward the proximal side with respect to the housing 100. Accordingly, the displacement shaft 33 moves from the initial position illustrated in FIGS. 3A and 3B to the compression position illustrated in FIGS. 4A and 4B, and the action portion 114 provided on the operation knob 110 presses the distal end of the elastic body 120 in the proximal direction. Therefore, the proximal end of the elastic body 120 presses the fixing member 170 toward the proximal direction, and the displacement shaft 33 fixed to the fixing member 170 moves toward the proximal direction. As a result, as illustrated in FIG. 11, the concave portions 55 of the expandable body 21 sandwich the biological tissue. At this time, the biological tissue surrounding the through-hole Hh is sandwiched between electrode portions 22 and the facing portions 82 and the biological tissue can be held (or grasped) relatively well. The operation knob 110 applies a pulling force to the displacement shaft 33 via the elastic body 120. Therefore, it is possible to help prevent the pulling force exceeding a force that can be supported from acting on the displacement shaft 33 by the elastic body 120. That is, when a force for sandwiching the biological tissue is likely to be excessive due to the expandable body 21, the elastic body 120 is contracted, and the compressive force for compressing the expandable body 21 in the axial direction can be automatically adjusted. As a result, the force sandwiching the biological tissue is automatically adjusted.

Figure 6A:
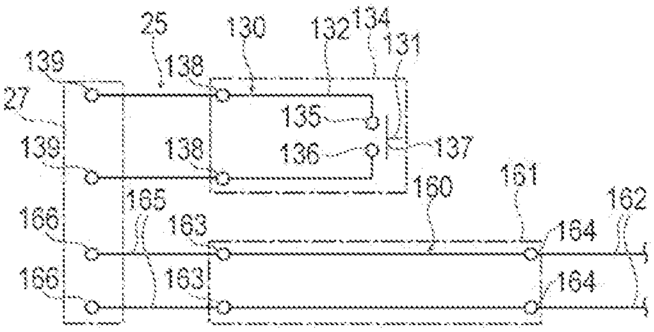
FIGS. 6A and 6B are circuit diagrams illustrating the switch mechanism of the medical device.
Figure 6B:
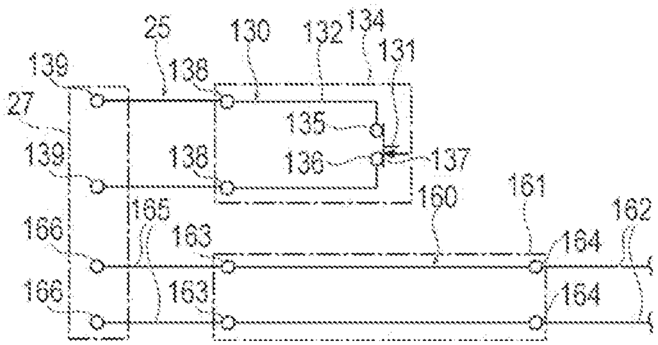

When the knob body 111 is moved toward the proximal side with respect to the housing 100 and the displacement shaft 33 is moved from the initial position to the compression position, as illustrated in FIGS. 4A and 4B, the contact portion 113 of the operation knob 110 moves from the non-contact position where the contact portion 113 is not in contact with the pressing portion 150 to the contact position where the contact portion 113 comes into contact with the pressing portion 150, and comes into contact with the press input portion 152 of the pressing portion 150. Accordingly, the press input portion 152 is pushed and moved by the contact portion 113, and rotates the pressing portion 150. When the pressing portion 150 is rotated, the press output portion 153 changes from the non-pressing state in which the switch main body 133 of the detection switch 131 is not pressed to the pressing state in which switch main body 133 is pressed, and pushes the switch main body 133. Accordingly, as illustrated in FIGS. 6A and 6B, the movable contact 137 disposed on the switch main body 133 is brought into contact with both the first fixed contact 135 and the second fixed contact 136, and is electrically connected with both the first fixed contact 135 and the second fixed contact 136. Accordingly, the current input to the input unit 194 electrically connected to the first fixed contact 135 and the second fixed contact 136 changes, and the control unit 193 (see FIG. 1) can determine that the displacement shaft 33 reaches the compression position and the expandable body 21 is compressed in the axial direction, based on a change in a resistance value between the first fixed contact 135 and the second fixed contact 136.

When the first fixed contact 135 and the second fixed contact 136 are electrically connected, the control unit 193 determines that the displacement shaft 33 reaches the compression position, changes the electric power output unit 191 from the pause mode to the output mode in which electric power for cauterization can be output, and causes the notification unit 192 (see FIG. 1) to provide information indicating that the electric power output unit 191 is changed to the output mode.

Next, in S6, the surgeon performs the maintenance treatment in order to maintain the size of the through-hole Hh. In the maintenance treatment, by applying high-frequency energy to an edge portion of the through-hole Hh through the electrodes 24, the edge portion of the through-hole Hh is cauterized (cauterized by heating) using the high-frequency energy. Based on the information obtained by the notification unit 192, the surgeon recognizes that the electric power output unit 191 is in the output mode and is in a state in which the electric power can be output, and causes the electric power output unit 191 to output electric power through an interface such as a keyboard, a mouse, or a dedicated button connected to the control unit 193.

When the biological tissue in the vicinity of the edge portion of the through-hole Hh is cauterized through the electrodes 24, a denatured portion where the biological tissue is denatured is formed in the vicinity of the edge portion. Since the biological tissue at the denatured portion is in a state in which the biological tissue loses elasticity, the shape of the through-hole Hh at the time of being pressed to be spread by the expandable body 21 can be maintained. Since the through-hole Hh is held at an appropriate size by the expandable body 21 provided with a buffer portion and is cauterized, the shape is maintained at the appropriate size. Accordingly, the through-hole Hh can be used as a shunt.

After the completion of S6, the surgeon reduces the diameter of the expandable body 21, houses the expandable body 21 in the outer tube 30, and then removes the outer tube 30 from the through-hole Hh. Further, the entire medical device 10 is removed to the outside of the living body, and the treatment is completed.

As described above, the medical device 10 according to the present embodiment can include: the expandable body 21 that has a central axis and that is expandable and contractible in a radial direction; the elongated shaft portion 31 connected to the expandable body 21; the energy transmission element 22 provided along the expandable body 21; the housing 100 connected to the proximal end portion of the shaft portion 31; the elongated displacement shaft 33 that is relatively displaced from the initial position to the compression position with respect to the shaft portion 31 along the axial direction of the expandable body 21 so as to compress the expandable body 21 in the axial direction; the operation knob 110 that is movable with respect to the housing 100; the detection unit 130 housed in the housing 100 and configured to detect the compression of the expandable body 21 caused by the displacement shaft 33; and the electric wire 160 connectable to the electric power supply device 190 that supplies electric power to the energy transmission element 22, and configured to pass through the housing 100 and extend to the energy transmission element 22 along the shaft portion 31. The expandable body 21 includes: the concave portions 55 recessed inward in the radial direction at an intermediate portion in the axial direction; the first connection portion 54 connected to the shaft portion 31; and the second connection portion 53 facing the first connection portion 54 with the concave portions 55 interposed between the second connection portion 53 and the first connection portion 54 in the axial direction. The displacement shaft 33 extends from inside the housing 100 along the shaft portion 31 and is connected to the second connection portion 53 of the expandable body 21. The concave portions 55 include, in order to define the receiving space 74 capable of receiving the biological tissue, the distal erected sections 72, the proximal erected sections 73, and the bottom sections 71 located on the innermost side in the radial direction and disposed between the distal erected sections 72 and the proximal erected sections 73. The distal erected sections 72 and the proximal erected sections 73 grip (or grasp) the biological tissue by the displacement of the displacement shaft 33 from the initial position to the compression position. The energy transmission element 22 is disposed along any one of the distal erected sections 72 and the proximal erected sections 73 in a manner of facing the receiving space 74. The operation knob 110 can include: the knob body 111 that protrudes from the housing 100, and that moves and operates the operation knob 110 with respect to the housing 100; and the action portion 114 movably disposed in the housing 100 and configured to act on the proximal end portion of the displacement shaft 33 housed in the housing 100 according to the movement and the operation of the operation knob 110, and cause the displacement shaft 33 to be displaced from the initial position to the compression position. The detection unit 130 can include: the detection switch 131 configured to switch the state according to the displacement of the displacement shaft 33 form the initial position to the compression position caused by the operation knob 110; and the output unit 132 configured to output the state change of the detection switch 131 to the electric power supply device 190. The detection switch 131 and the output unit 132 are electrically independent from the electric wire 160.

In the medical device 10 implemented as described above, the compression of the expandable body 21 due to the movement of the displacement shaft 33 from the initial position to the compression position when the operation knob 110 is moved with respect to the housing 100 can be detected by the detection unit 130, and can be output to the electric power supply device 190. Therefore, since the electric power supply device 190 can determine whether the operation knob 110 is operated, it is possible to reduce the supply of the energy to the energy transmission element 22 in a state in which the operation of pressing the energy transmission element 22 against the biological tissue is not performed. Therefore, it is possible to reduce a risk that a thrombus is formed by the energy transmission element 22 being exposed to blood, or that an unintended part is damaged by the energy transmission element 22. Further, in the medical device 10, since the detection switch 131 and the output unit 132 are independent from the electric wire 160 that supplies the energy for cauterization, a circuit from the electric power output unit 191 to the energy transmission element 22 is not directly turned ON or OFF. Therefore, it is possible to reduce a risk of firing due to a contact failure and a risk of electric leakage, and to check whether the circuit for cauterization from the electric power output unit 191 to the energy transmission element 22 is short-circuited.

The medical device 10 can further include: the connection terminal 27 capable of being connected to the electric power supply device 190; and the circuit board housed in the housing 100. The connection terminal 27 includes the first terminals 166 and the second terminals 139 that are electrically independent from each other. The electric wire 160 can include: the supply circuit 161 capable of being connected to the electric power supply device 190 via the first terminals 166 and disposed on the circuit board; the electric wire main bodies 162 configured to extend from the supply circuit 161 to the energy transmission element 22 along the shaft portion 31; and the connecting electric wire portions 165 configured to extend from the supply circuit 161 to the first terminals 166. The output unit 132 is capable of outputting the state change of the detection switch 131 to the electric power supply device 190 via the second terminals 139, and can include, on the circuit board, the output circuit 134 electrically independent from the supply circuit 161. The detection switch 131 can include: the switch main body 133 configured to change the state of the detection switch 131 by being pressed; and the pressing portion 150 configured to press the switch main body 133. The pressing portion 150 is displaceable between the pressing state in which the switch main body 133 is pressed and the non-pressing state in which the switch main body 133 is not pressed according to the operation of the operation knob 110 for moving the displacement shaft 33 from the initial position to the compression position. Accordingly, the operation of the operation knob 110 is indirectly transmitted to the switch main body 133 via the pressing portion 150. By integrating the supply circuit 161 and the output circuit 134 on one circuit board and integrating the first terminals 166 and the second terminals 139 into one connection terminal 27, wiring and soldering become relatively easy. Further, by adopting a structure in which the pressing portion 150 is disposed between the operation knob 110 and the switch main body 133, it is no longer necessary to provide a positional limitation that the operation knob 110 is disposed at a position where the operation knob 110 can be brought into contact with the switch main body 133, and the degree of design freedom can be improved. Therefore, it becomes relatively easy to implement a structure having a desired function in a limited space.

The action portion 114 of the operation knob 110 can include the contact portion 113 disposed in the housing 100, the contact portion 113 is displaced between the non-contact position where the contact portion 113 is not in contact with the pressing portion 150 and the contact position where the contact portion 113 is in contact with the pressing portion 150 due to the operation of the operation knob 110 for moving the displacement shaft 33 from the initial position to the compression position, and the pressing portion 150 is brought into the pressing state by being brought into contact with the contact portion 113. Accordingly, it is possible to effectively shift the pressing portion 150 from the non-pressing state to the pressing state using the position change of the contact portion 113 according to the movement of the operation knob 110 in the axial direction.

The action portion 114 of the operation knob 110 is connected to the proximal end portion of the displacement shaft 33, is movable from the first position to the second position along the axial direction of the displacement shaft 33, and moves the displacement shaft 33 from the initial position to the compression position according to the movement from the first position to the second position. Accordingly, it is possible to move the displacement shaft 33 from the initial position to the compression position by the movement of the operation knob 110 along the axial direction.

The first connection portion 54 of the expandable body 21 is located at a proximal side with respect to the second connection portion 53. The displacement shaft 33 compresses the expandable body 21 in the axial direction by pulling the second connection portion 53 in the proximal direction according to the movement from the initial position to the compression position located at the proximal side with respect to the initial position. The action portion 114 of the operation knob 110 causes the displacement shaft 33 to move from the initial position to the compression position according to the movement from the first position to the second position located at the proximal side with respect to the first position. Accordingly, by an operation of positioning the operation knob 110 at the proximal side, the second connection portion 53 disposed at the distal side with respect to the first connection portion 54 of the expandable body 21 can be pulled in the proximal direction via the displacement shaft 33, and the expandable body 21 can be effectively compressed in the axial direction.

The disclosure may also provide the medical system 1. The medical system 1 can include the above medical device 10 and the electric power supply device 190. Accordingly, since the medical system 1 can determine whether the operation knob 110 is operated by the electric power supply device 190, it is possible to reduce the supply of the energy to the energy transmission element 22 in the state in which the operation of pressing the energy transmission element 22 against the biological tissue is not performed. Therefore, it is possible to reduce a risk that a thrombus is formed by the energy transmission element 22 being exposed to blood, or that an unintended part is damaged by the energy transmission element 22.

The electric power supply device 190 can include: the input unit 194 configured to receive the state change of the detection switch 131 output from the output unit 132; the electric power output unit 191 configured to output electric power to the energy transmission element 22 via the electric wire 160; and the control unit 193 configured to control output of the electric power from the electric power output unit 191. The electric power output unit 191 has the output mode in which electric power is capable of being output and the pause mode in which electric power is not capable of being output, and the control unit 193 changes the electric power output unit 191 from the pause mode to the output mode when the state change of the detection switch 131 corresponding to the compression of the expandable body 21 is received by the input unit 194. Accordingly, the electric power supply device 190 can determine whether the operation knob 110 is operated based on the information obtained from the output unit 132 of the medical device 10, and can change the electric power output unit 191 from the pause mode to the output mode. Since the energy can be supplied from the electric power supply device by the electric power output unit 191 changing from the pause mode to the output mode, it is possible to reliably reduce the supply of the energy to the energy transmission element 22 in the state in which the operation of pressing the energy transmission element 22 against the biological tissue is not performed.

Figure 13A:
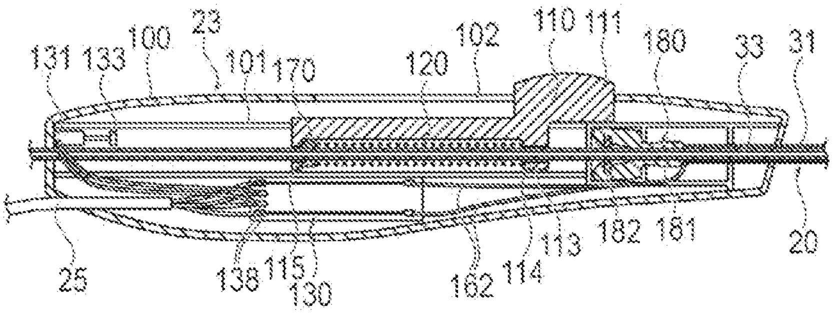
FIGS. 13A and 13B are longitudinal sectional views of an inside of an operation unit according to a first modification.
Figure 13B:
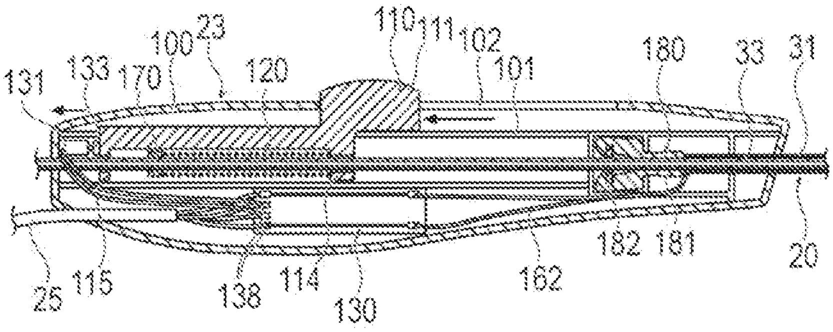

Note that the disclosure is not limited to the embodiment described above, and various modifications can be made by a person skilled in the art within a scope of the technical idea of the disclosure. Therefore, in the above embodiment, when the operation knob 110 moves and the switch main body 133 of the detection switch 131 is pressed via the pressing portion 150, the electric power output unit 191 changes from the pause mode to the output mode. In a first modification as illustrated in FIGS. 13A and 13B, the electric power output unit 191 may change from the pause mode to the output mode by the operation knob 110 moving and the operation knob 110 directly pressing the switch main body 133.

Figure 14A:
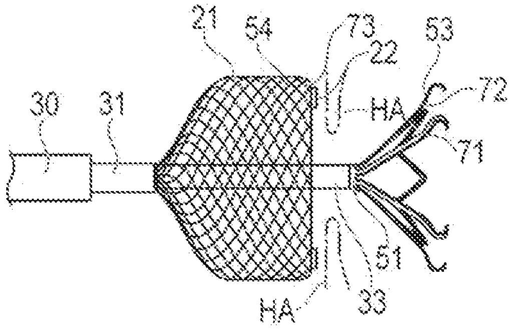
FIGS. 14A and 14B are plan views illustrating a distal end portion of a medical device according to a second modification.
Figure 14B:
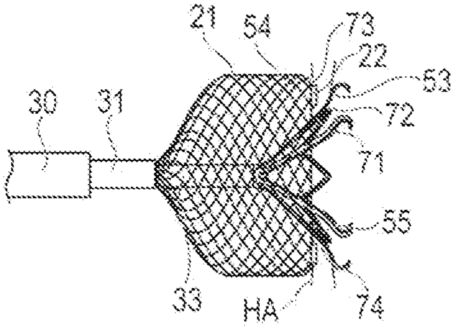

Further, as in a second modification illustrated in FIGS. 14A and 14B, the second connection portion 53 and the first connection portion 54 of the expandable body 21 may have another structure. The distal erected sections 72 and the bottom sections 71 are disposed in the second connection portion 53, and the proximal erected section 73 is disposed in the first connection portion 54. The distal erected sections 72, the bottom sections 71 and the proximal erected section 73 define the receiving space 74 of the concave portions 55. The bottom sections 71 may be disposed in the first connection portion 54. The energy transmission element 22 is disposed in the first connection portion 54, and may be disposed in the second connection portion 53. The first connection portion 54 and the second connection portion 53 are accommodated in the outer tube 30 in a state of being elastically deformed and contracted, and are expanded by an elastic expansion force (restoring force) of the first connection portion 54 and the second connection portion 53 by being exposed from the outer tube 30. The shaft portion 31 is fixed to a proximal end of the first connection portion 54, and the displacement shaft 33 is fixed to a proximal end of the second connection portion 53. The displacement shaft 33 is slidable inside the shaft portion 31. Therefore, the displacement mechanism that compresses the expandable body 21 in the axial direction is a mechanism that pulls the displacement shaft 33 toward the proximal side or that presses the shaft portion 31 toward the distal side. By operating the displacement mechanism, as illustrated in FIG. 14B, the distal erected sections 72 and the proximal erected section 73 come relatively close to each other to reduce the receiving space 74, and it is possible to grip (or grasp) the atrial septum HA, which is the biological tissue, between the distal erected sections 72 and the proximal erected section 73.

The detection switch 131 may have a structure in which an OFF state may be detected when the conduction of the switch is always ON, instead of detecting an ON state when the conduction of the switch is always OFF.

The detailed description above describes embodiments of a medical device and a medical system that include an expandable body in which an energy transmission element that is inserted into a living body and that cauterizes a biological tissue. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:

an expandable body having a central axis and configured to be expandable and contractible in a radial direction;

an elongated shaft portion configured to be connected to the expandable body;

an energy transmission element provided along the expandable body;

a housing configured to be connected to a proximal end portion of the shaft portion;

an elongated displacement shaft configured to be relatively displaced from an initial position to a compression position with respect to the shaft portion along an axial direction of the expandable body and configured to compress the expandable body in the axial direction;

an operation knob configured to be movable with respect to the housing;

a detection unit housed in the housing and configured to detect compression of the expandable body caused by the displacement shaft;

an electric wire configured to be connected to an electric power supply device configured to supply electric power to the energy transmission element, and configured to pass through the housing and extend to the energy transmission element along the shaft portion;

the expandable body includes a concave portion recessed inward in the radial direction at an intermediate portion in the axial direction, a first connection portion connected to the shaft portion, and a second connection portion facing the first connection portion with the concave portion interposed between the second connection portion and the first connection portion in the axial direction;

the displacement shaft extends from inside the housing along the shaft portion and is connected to the second connection portion of the expandable body;

the concave portion includes, in order to define a receiving space configured to receive a biological tissue, a distal erected section, a proximal erected section, and a bottom section located on an innermost side in the radial direction and disposed between the distal erected section and the proximal erected section;

the distal erected section and the proximal erected section configured to grip the biological tissue by the displacement of the displacement shaft from the initial position to the compression position;

the energy transmission element is disposed along one of the distal erected section and the proximal erected section in a manner of facing the receiving space;

the operation knob includes a knob body that protrudes from the housing and an action portion, the knob body configured to move and operate the operation knob with respect to the housing, the action portion configured to be movably disposed in the housing and configured to act on the proximal end portion of the displacement shaft housed in the housing according to the movement and the operation of the operation knob and to cause the displacement shaft to be displaced from the initial position to the compression position;

the detection unit includes a detection switch configured to switch a state according to the displacement of the displacement shaft from the initial position to the compression position caused by the operation knob, and an output unit configured to output a state change of the detection switch to the electric power supply device; and wherein the detection switch and the output unit are electrically independent from the electric wire.

2. The medical device according to claim 1, further comprising:

a connection terminal capable of being connected to the electric power supply device;

a circuit board housed in the housing;

the connection terminal includes a first terminal and a second terminal that are electrically independent from each other;

the electric wire includes a supply circuit capable of being connected to the electric power supply device via the first terminal and disposed on the circuit board, an electric wire main body configured to extend from the supply circuit to the energy transmission element along the shaft portion, and a connecting electric wire portion configured to extend from the supply circuit to the first terminal;

the output unit is configured to output the state change of the detection switch to the electric power supply device via the second terminal, and includes, on the circuit board, an output circuit electrically independent from the supply circuit;

the detection switch includes a switch main body configured to change a state of the detection switch by being pressed, and a pressing portion configured to press the switch main body; and the pressing portion is configured to be displaceable between a pressing state in which the switch main body is pressed and a non-pressing state in which the switch main body is not pressed according to an operation of the operation knob for moving the displacement shaft from the initial position to the compression position.

3. The medical device according to claim 1, wherein the action portion of the operation knob includes a contact portion disposed in the housing;

the contact portion is displaced between a non-contact position where the contact portion is not in contact with the pressing portion and a contact position where the contact portion is in contact with the pressing portion due to the operation of the operation knob for moving the displacement shaft from the initial position to the compression position; and the pressing portion is brought into the pressing state by being brought into contact with the contact portion.

4. The medical device according to claim 1, wherein the action portion of the operation knob is connected to the proximal end portion of the displacement shaft, the action portion of the operation knob being configured to be movable from a first position to a second position along the axial direction of the displacement shaft, and configured to move the displacement shaft from the initial position to the compression position according to the movement from the first position to the second position.

5. The medical device according to claim 1, wherein the first connection portion of the expandable body is located at a proximal side with respect to the second connection portion;

the displacement shaft is configured to compress the expandable body in the axial direction by pulling the second connection portion in a proximal direction according to a movement from the initial position to the compression position located at the proximal side with respect to the initial position; and the action portion of the operation knob is configured to cause the displacement shaft to move from the initial position to the compression position according to a movement from the first position to the second position located at the proximal side with respect to the first position.

6. A medical system comprising:

the medical device according to claim 1; and the electric power supply device.

7. The medical system according to claim 6, wherein the electric power supply device includes:

an input unit configured to receive the state change of the detection switch output from the output unit;

an electric power output unit configured to output electric power to the energy transmission element via the electric wire; and a control unit configured to control output of the electric power from the electric power output unit;

the electric power output unit includes an output mode in which electric power is configured to be output and a pause mode in which electric power is not configured to be output; and the control unit is configured to change the electric power output unit from the pause mode to the output mode when the state change of the detection switch corresponding to the compression of the expandable body is received by the input unit.

8. A treatment method to widen a through-hole in biological tissue comprising:

disposing the expandable body of the medical device of claim 1 in the through-hole;

receiving the biological tissue in the receiving space;

checking hemodynamics in the vicinity of the through-hole;

gripping the through-hole with the expandable body;

performing a maintenance treatment for maintaining the size of the through-hole; and checking the hemodynamics in the vicinity of the through-hole after the maintenance treatment is performed.

9. A medical device comprising:

an expandable body having a central axis and configured to be expandable and contractible in a radial direction;

an elongated shaft portion configured to be connected to the expandable body;

an energy transmission element provided along the expandable body;

a housing configured to be connected to a proximal end portion of the shaft portion;

an elongated displacement shaft configured to be relatively displaced from an initial position to a compression position with respect to the shaft portion along an axial direction of the expandable body and configured to compress the expandable body in the axial direction;

an operation knob configured to be movable with respect to the housing; and a detection unit housed in the housing and configured to detect compression of the expandable body caused by the displacement shaft, the detection unit includes a detection switch configured to switch a state according to the displacement of the displacement shaft from the initial position to the compression position caused by the operation knob, and an output unit configured to output a state change of the detection switch to an electric power supply device.

10. The medical device according to claim 9, further comprising:

an electric wire connectable to the electric power supply device configured to supply electric power to the energy transmission element, and configured to pass through the housing and extend to the energy transmission element along the shaft portion.

11. The medical device according to claim 10, further comprising:

the operation knob includes a knob body that protrudes from the housing and an action portion, the knob body configured to move and operate the operation knob with respect to the housing, the action portion configured to be movably disposed in the housing and configured to act on the proximal end portion of the displacement shaft housed in the housing according to the movement and the operation of the operation knob and to cause the displacement shaft to be displaced from the initial position to the compression position.

12. The medical device according to claim 11, wherein the action portion of the operation knob includes a contact portion disposed in the housing;

the contact portion is displaced between a non-contact position where the contact portion is not in contact with the pressing portion and a contact position where the contact portion is in contact with the pressing portion due to the operation of the operation knob for moving the displacement shaft from the initial position to the compression position; and the pressing portion is brought into the pressing state by being brought into contact with the contact portion.

13. The medical device according to claim 11, wherein the action portion of the operation knob is connected to the proximal end portion of the displacement shaft, the action portion is configured to be movable from a first position to a second position along the axial direction of the displacement shaft, and configured to move the displacement shaft from the initial position to the compression position according to the movement from the first position to the second position.

14. The medical device according to claim 9, wherein the detection switch and the output unit are electrically independent from the electric wire.

15. The medical device according to claim 9, further comprising:

a connection terminal capable of being connected to the electric power supply device;

a circuit board housed in the housing;

the connection terminal includes a first terminal and a second terminal that are electrically independent from each other; and the electric wire includes a supply circuit capable of being connected to the electric power supply device via the first terminal and disposed on the circuit board, an electric wire main body configured to extend from the supply circuit to the energy transmission element along the shaft portion, and a connecting electric wire portion configured to extend from the supply circuit to the first terminal.

16. The medical device according to claim 15, wherein the output unit is configured to output the state change of the detection switch to the electric power supply device via the second terminal, and includes, on the circuit board, an output circuit electrically independent from the supply circuit.

17. The medical device according to claim 9, wherein the detection switch includes a switch main body configured to change a state of the detection switch by being pressed, and a pressing portion configured to press the switch main body; and the pressing portion is configured to be displaceable between a pressing state in which the switch main body is pressed and a non-pressing state in which the switch main body is not pressed according to an operation of the operation knob for moving the displacement shaft from the initial position to the compression position.

18. The medical device according to claim 9, wherein the displacement shaft is configured compress the expandable body in the axial direction in a proximal direction according to a movement from the initial position to the compression position located at the proximal side with respect to the initial position; and the action portion of the operation knob is configured to cause the displacement shaft to move from the initial position to the compression position according to a movement from the first position to the second position located at the proximal side with respect to the first position.

19. An operation unit for use in cauterization of a biological tissue, the operation unit comprising:

a housing;

an operation knob configured to be movable with respect to the housing;

a detection unit housed in the housing configured to detect compression of an expandable body caused by a displacement shaft;

an electric wire connectable to an electric power supply device configured to supply electric power to the energy transmission element, and configured to pass through the housing and extend to an energy transmission element along a shaft portion connected to the expandable body;

the operation knob includes a knob body that protrudes from the housing and an action portion, the knob body configured to move and operate the operation knob with respect to the housing, the action portion configured to be movably disposed in the housing and configured to act on a proximal end portion of the displacement shaft housed in the housing according to the movement and the operation of the operation knob and to cause the displacement shaft to be displaced from the initial position to the compression position; and the detection unit includes a detection switch configured to switch a state according to the displacement of the displacement shaft from the initial position to the compression position caused by the operation knob, and an output unit configured to output a state change of the detection switch to the electric power supply device.

20. The operation unit according to claim 19, wherein the detection switch and the output unit are electrically independent from the electric wire.

* * * * *